US00PP15774P3

(12) United States Plant Patent
Bourne

(10) Patent No.: US PP15,774 P3
(45) Date of Patent: May 24, 2005

(54) GRAPEVINE PLANT NAMED '14-48-258'

(50) Latin Name: *Vitis vinifera*
Varietal Denomination: 14-48-258

(75) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 450 days.

(21) Appl. No.: 10/295,253

(22) Filed: Nov. 15, 2002

(65) Prior Publication Data

US 2004/0098772 P1 May 20, 2004

(51) Int. Cl.[7] ..... A01H 5/00

(52) U.S. Cl. ..... Plt./205

(58) Field of Search ..... Plt./205

*Primary Examiner*—Kent Bell
(74) *Attorney, Agent, or Firm*—Jondle & Associates, PC

(57) ABSTRACT

This new seeded variety of grape '14-48-258' is new and different because of its firm texture, uniform clusters and large berry size. Its clusters are well-filled, but loose; its large berries are sweet and mild. The vigorously growing vines are extremely productive when spur pruned.

2 Drawing Sheets

Genus and species: *Vitis vinifera.*

BACKGROUND AND SUMMARY OF THE INVENTION

The new grape plant named '14-48-258' is of *Vitis vinifera* parentage. The goal in the development of this new table grape was to provide an alternative to the widely grown cultivar 'Alphonse Lavalle' (unpatented).

The female parent of the new variety is an un-named (unpatented) black table grape of uncertain parentage with large berry size and high fruitfulness. The seedless, male parent of the new cultivar is the variety 'Fantasy Seedless' (unpatented). The hybridization resulting in the new cultivar was made in 1993 near Delano, Calif. Seed from the cross was harvested, stratified and sown in a greenhouse in January 1994. The resulting 47 seedlings were planted in a field in the same area in March of the same year. In 1997, fruit was seen on the instant vine for the first time and it was selected for further trial. Vines were propagated from the original seedling near Delano, Calif. in the spring of 1998 with own-rooted and grafted vines planted in the original trial. Those vines and subsequent propagules have all been true to type.

COMPARISON WITH PARENTAL CULTIVAR

The new cultivar differs from its female parent by having much larger berries and greater fruitfulness. It differs from its male parent, Fantasy seedless, by having seeded rather than Seedless berries.

DESCRIPTION OF THE FIGURES

The accompanying drawings illustrate the following.

DETAILED BOTANICAL DESCRIPTION OF THE INVENTION

Figure 1:
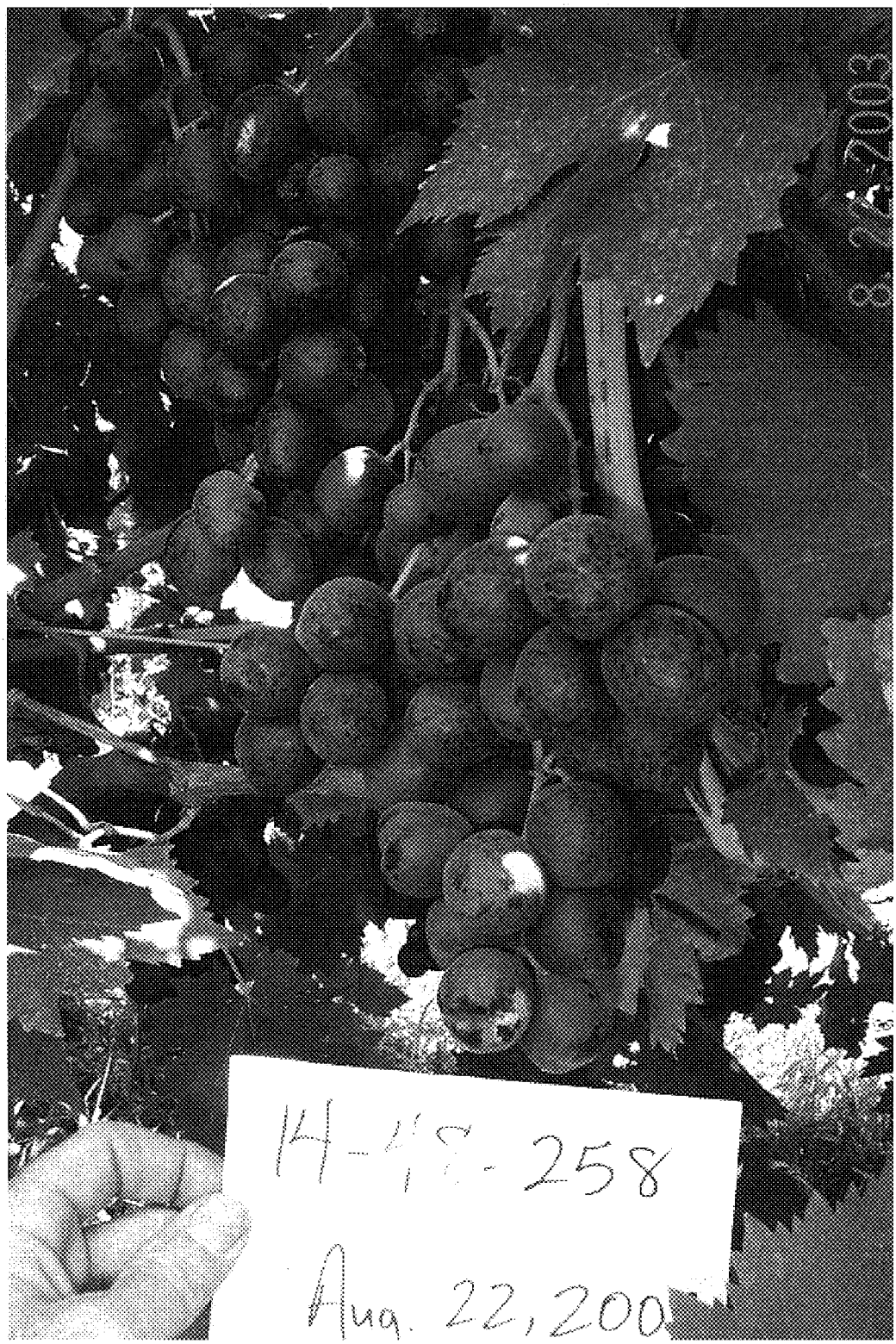
FIG. 1 shows a fruit cluster at harvest.
Figure 2:
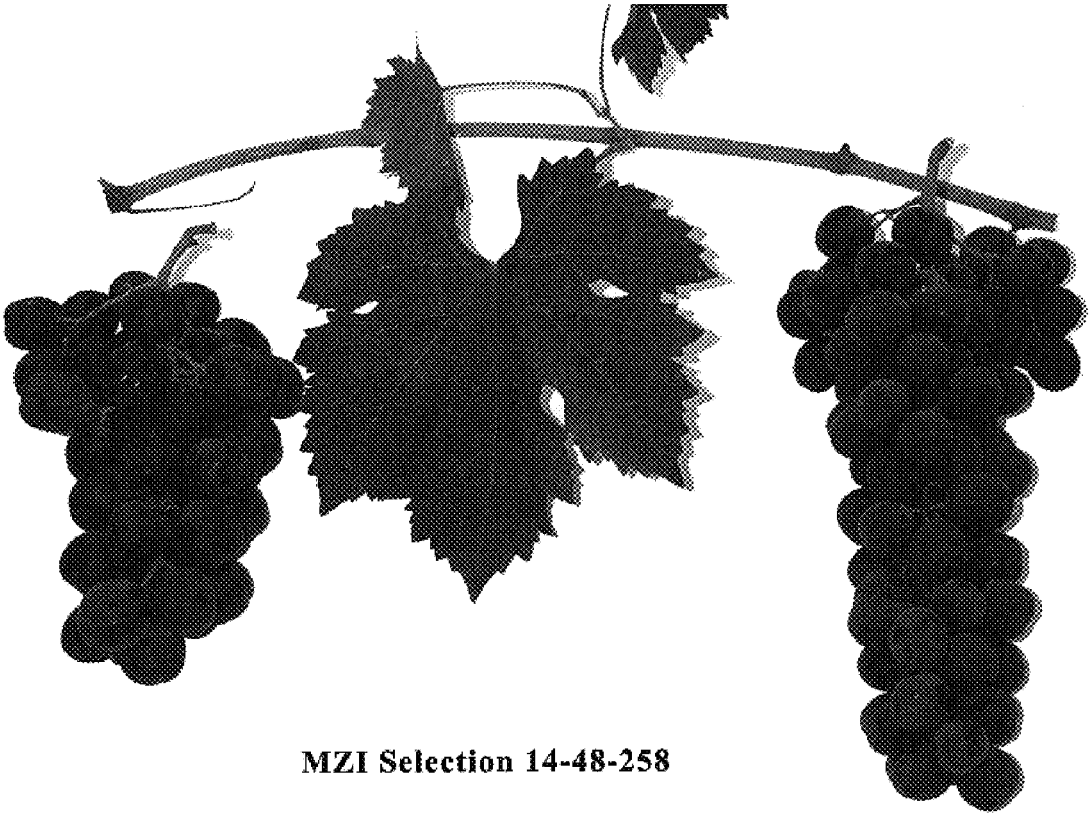
FIG. 2 shows the cane, Leaf, natural fruit cluster (right), and cluster following trimming and cluster thinning.

The following description of grapevine '14-48-258' contains references to color names taken from The Munsell Color Chart for Plant Tissues, published by Munsell Color, New Windsor, N.Y. Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in Descriptors for Grapevine (*Vitis* spp.) (Anonymous, International Plant Genetic Resources Institute, 1997, ISBN 92-9043-352-3).

Descriptions of the new invention apply to vines of '14-48-258' grown on 'Freedom' (unpatented) rootstock at a density of 1,537 vines per hectare grown in Kern County, Calif. in 2001. These vines were in their first year of full production having been planted in 1998. These descriptions are believed to apply generally to the new variety grown under similar circumstances elsewhere:

VINE

General:

*Vigor.*—Medium, vines spur pruned and thinned to 32 shoots per cluster average 241.3 cm. of growth per cane.

*Density of foliage.*—Dense.

*Productivity.*—Very productive when spur pruned, up to 64,157 kg./hectare.

*Hardiness.*—Hardiness observed to 0 C.

*Rootstock.*—Freedom.

Trunk:

*Shape.*—Broadly elliptical.

*Straps.*—Long, split.

*Surface texture.*—Shaggy.

*Inner bark color.*—5YR 4/6.

*Outer bark color.*—7.5 YR 6/2.

*Trunk circumference.*—15.4 cm. at 1 meter height.

LEAVES

Mature leaves:
*Average blade length.*—16.0 cm.
*Average blade width.*—22.5 cm.
*Size of blade.*—Large.
*Shape.*—Pentagonal.
*Anthocyanin coloration of main veins on the upper side of the blade.*—Strong, 2.5R 4/10.
*Mature leaf profile.*—Wavy.
*Blistering surface of blade upper surface.*—Absent.
*Leaf blade tip.*—In plane of the leaf.
*Margins.*—Lobed, serrate, undulating.
*Apex.*—Acuminate.
*Base.*—Sagittate.
*Thickness.*—Medium.
*Undulation of blade between main and lateral veins.*—Strong.
*Shape of teeth.*—Conical, both sides convex.
*Length of teeth.*—3–10 mm.
*Ratio length/width of teeth.*—About 1:1.
*General shape of petiole sinus.*—Variable — open (ovate) to closed.
*Tooth at petiole sinus.*—Absent.
*Petiole sinus limited by veins.*—Absent.
*Shape of upper lateral sinus.*—Closed.
*Prostrate hairs between veins on lower surface of blade.*—Absent.
*Erect hairs between veins on lower surface of blade.*—Absent.
*Prostrate hairs on main veins on lower surface of blade.*—Absent.
*Density of erect hairs on main veins on lower surface of blade.*—Sparse, confined to junction of veins.
*Prostrate hairs on main veins on upper surface of blade.*—Absent.

Upper surface:
*Summer color.*—7.5 GY 4/4 to 3/4.
*Autumn color.*—5Y 8/8.
*Surface texture.*—Smooth.
*Surface appearance.*—Dull.
*Goffering of blade.*—Absent.

Lower surface:
*Summer color.*—7.5GY 4/6.
*Autumn color.*—5Y 8/6.
*Anthocyanin coloration of main veins on lower leaf surface.*—Present.
*Glossiness.*—Low.
*Pubescence.*—Absent.
*Surface texture.*—Smooth.
*Surface appearance.*—Dull.

Petiole:
*Length of petiole.*—16.2 cm.
*Length of petiole compared to middle vein.*—Approximately equal.
*Density of prostrate hairs on petiole.*—Absent.
*Density of erect hairs on petiole.*—Absent.
*Shape of base of petiole sinus.*—Mostly closed, some ½ open, ovate.
*Diameter.*—3 mm.
*Color.*—5GY 6/6 with red streaks 5RP 4/8.

TENDRILS

Number: Forming at most nodes between nodes 5–12. Few thereafter.
*Length.*—24.3 cm.
*Diameter.*—2 mm.
*Texture.*—Smooth.
*Color.*—5GY 7/8.

WOODY SHOOT

Canes:
*Shape.*—Circular to broadly elliptical in cross section.
*Internode length.*—About 9.5 cm.
*Width at node.*—About 2.0 cm.
*Cross section.*—Circular.
*Surface.*—Smooth.
*Main color.*—5YR 5/6.
*Lenticels.*—Inconspicuous.
*Erect hairs on nodes.*—Absent.
*Erect hairs on internodes.*—Absent.
*Growth of axillary shoots.*—Prolific.

Laterals:
*Shape.*—Circular to broadly elliptical.
*Number.*—Laterals forming at almost all nodes above node 4.
*Length.*—7 cm.–63 cm.
*Diameter.*—2–6 mm.
*Internode length.*—2.5–8 cm.
*Color.*—7.5 YR 6/6–6/10.

Buds:
*Shape.*—Conical.
*Cane bud fruitfulness.*—Basal buds fruitful, 1–2 clusters per shoot.
*Length.*—4 mm.
*Width.*—4 mm.
*Height.*—4 mm.
*Color.*—5 YR 3/4.
*Time of bud burst.*—Mar. 21, 2003.

FLOWERS

General:
*Flower sex.*—Perfect.
*Length of first inflorescence.*—23.1 cm.
*Position of first flowering nodes.*—$3^{rd}$ to $4^{th}$.
*Number of inflorescences per shoot.*—1 or 2.
*Calyptra color.*—5GY 7/8.
*Ovary length.*—2 mm.
*Ovary width.*—1.5 mm.
*Ovary color.*—5GY 4/8.
*Filament length.*—2 mm.
*Filament color.*—2.5GY 8/2.
*Anther length.*—1 mm.
*Anther color.*—2.5GY 8/8.
*Date of full bloom.*—May 14, 2001 in McFarland, Calif.

FRUIT

General:
*Ripening period.*—Late, mid-season, about 3 weeks after 'Thompson Seedless' (unpatented) at Delano, Calif.
*Date of ripening.*—About September 1st .
*Use.*—Fresh market.
*Keeping quality.*—Very good.
*Resistance.*—Insects: typical of *Vitis vinifera*. Diseases: typical of *Vitis vinifera*.
*Shipping quality.*—Good.
*Date of first harvest.*—Sep. 1, 2001.
*Solids-sugar.*—About 20 brix at full maturity.
*Refractometer test.*—19.0 brix.

Cluster:

*Bunch size.*—Medium.

*Bunch length* (*peduncle excluded*).—About 30.0 cm.

*Bunch width.*—About 9.0 cm.

*Bunch weight* (*natural*).—1,392 g.

*Bunch density.*—Very dense.

*Number of berries.*—97.3.

*Form.*—Conical.

Peduncle:

*Length of peduncle.*—2.7 cm.

*Lignification of peduncle.*—Medium, upper 1 cm.

*Color.*—7.5YR 5/8.

Berry:

*Size.*—Large.

*Uniformity of size.*—Uniform.

*Berry weight.*—12.8 g.

*Shape.*—Obovate to elliptic.

*Presence of seeds.*—2–4 per berry, averaging 43 mg each; light brown, 2.5YR 4/6.

*Cross section.*—Circular.

*Dimensions.*—Longitudinal axis about 3.0 cm.; horizontal axis about 2.2 cm.

*Skin color* (*without bloom*).—Dark red-black, 5RP 3/2.

*Coloration of flesh.*—Translucent, 2.5GY 8/4.

*Juiciness of flesh.*—Very juicy.

*Berry firmness.*—Very firm.

*Particular flavor.*—Neutral, typical vinifera.

*Bloom* (*cuticular wax*).—Strong.

*Pedicel length.*—7 mm.

*Berry separation from pedicel.*—Moderate.

Skin:

*Thickness.*—Medium.

*Texture.*—Tender.

*Reticulation.*—Absent.

*Roughness.*—Absent.

*Tenacity.*—Tenacious to flesh.

*Tendency to crack.*—Resistant.

What is claimed is:

1. A new and distinct variety of grape plant named '14-48-258' as herein illustrated and described.

* * * * *

MZI Selection 14-48-258